United States Patent [19]
Angeletakis

[11] Patent Number: 5,979,805
[45] Date of Patent: Nov. 9, 1999

[54] VIBRATORY MILL AND METHOD OF USE FOR LOW CONTAMINATION GRINDING

[75] Inventor: Christos Angeletakis, Orange, Calif.

[73] Assignee: Kerr Corporation, Orangeburg, N.Y.

[21] Appl. No.: 09/205,901

[22] Filed: Dec. 4, 1998

Related U.S. Application Data

[63] Continuation-in-part of application No. 09/181,507, Oct. 28, 1998.

[51] Int. Cl.⁶ .............................. B02C 17/00; B02C 17/22
[52] U.S. Cl. .............................. 241/21; 241/27; 241/175; 241/182
[58] Field of Search .............................. 241/21, 170, 171, 241/175, 182, 184, 300, 27, 29

[56] References Cited

U.S. PATENT DOCUMENTS

| | | | |
|---|---|---|---|
| 3,100,088 | 8/1963 | Podmore et al. | 241/170 |
| 3,400,495 | 9/1968 | Balz | 241/175 |
| 3,422,577 | 1/1969 | McKibben | 241/175 |
| 3,514,907 | 6/1970 | Strom | 241/175 |
| 4,042,181 | 8/1977 | Huber et al. | 241/175 |
| 4,117,981 | 10/1978 | Engels | 241/46.15 |
| 4,129,261 | 12/1978 | Engels et al. | 241/46.11 |
| 4,544,359 | 10/1985 | Waknine | 523/115 |
| 5,065,946 | 11/1991 | Nishida et al. | 241/16 |
| 5,335,867 | 8/1994 | Stehr et al. | 241/69 |
| 5,593,097 | 1/1997 | Corbin | 241/21 |
| 5,610,712 | 3/1997 | Schmitz et al. | 356/335 |

OTHER PUBLICATIONS

ASM International, *Engineered Materials Handbook*, 1995, p. 742.

*Primary Examiner*—John M. Husar
*Attorney, Agent, or Firm*—Wood, Herron & Evans, L.L.P.

[57] ABSTRACT

The present invention provides a vibratory mill having a grinding chamber, preferably coated with an abrasion resistant polymer, the grinding chamber being charged with glass beads having a diameter in the range of about 0.1 mm to about 10.00 mm. There is further provided a method of using this mill to provide substantially pure ground dental filler particles having an average particle size less than the average wavelength of visible light.

9 Claims, 3 Drawing Sheets

VIBRATORY MILL AND METHOD OF USE FOR LOW CONTAMINATION GRINDING

This application is a continuation-in-part of U.S. patent application Ser. No. 09/181,507 filed Oct. 28, 1998, and entitled "Optimum Particle Sized Hybrid Composite", now pending which is incorporated by reference herein in its entirety.

FIELD OF THE INVENTION

The present invention is generally related to an improved vibratory mill, and more particularly to a vibratory mill and method of use for grinding submicron-sized reinforcing particulate having high purity suitable for use in a dental composite. Uniformly dispersed in the dental composite, the high purity submicron-sized reinforcing particulate provides high strength, improved wear resistance and gloss retention in clinical use.

BACKGROUND OF THE INVENTION

In dentistry, practitioners use a variety of restorative materials in order to create crowns, veneers, direct fillings, inlays, onlays and splints. Composite resins are a type of restorative material which are suspensions of strengthening agents, such as mineral filler particles, in a polymerizable resin matrix. These materials may be dispersion reinforced or particulate reinforced, depending on the type of filler, or may be hybrid composites or flowable composites, depending on the filler loading. A full discussion of these materials is included in U.S. patent application Ser. No. 09/181,507, entitled "Optimum Particle Sized Hybrid Composite," C. Angeletakis, et al., filed on Oct. 28, 1998 now pending (incorporated herein by reference in its entirety). Highly pure submicron particles are useful in these composite resin materials because they impart the desirable optical properties of high gloss and high translucency.

While agitator ball mills are known for producing submicron particles, they have previously not been used to produce particles for filler in dental composites because of the impurities which result. The inclusion of impurities in dental composites can decrease translucency and negatively affect color. Prior art mills are set forth in U.S. Pat. Nos. 5,335,867; 4,129,261; and 4,117,981, all assigned to Draiswerke GmbH and each incorporated herein by reference in its entirety; and 5,065,946, assigned to Matsushita Electric Industrial Co. and incorporated herein by reference in its entirety. These prior art mills typically include ceramic or metallic agitators and grinding chambers. During milling, the ceramic or metallic material of the agitator and grinding chamber spalls and abrades, and the abraded particles become intimately mixed with the material being ground. In the case of fillers for dental restoratives, these abraded particles are unacceptable due to their impact on the optical properties of the restorative. The abraded particles may cause decreased translucency due to light scattering and may impart an unnatural color. Draiswerke, Inc., Mahwah, N.J., has applied a polyurethane coating on the agitator and grinding chamber for their PML-H/V machine. The pigment from this coating, however, also contaminates the composites, making them unacceptable for dental use.

The predominant types of milling methods are dry milling and wet milling. In dry milling, air or an inert gas is used to keep particles in suspension. However, fine particles tend to agglomerate in response to van der Waals forces which limits the capabilities of dry milling. Wet milling uses a liquid such as water or alcohol to control reagglomeration of fine particles. Therefore, wet milling is typically used for comminution of submicron-sized particles.

A wet mill typically includes spherical media that apply sufficient force to break particles that are suspended in a liquid medium. Milling devices are categorized by the method used to impart motion to the media. The motion imparted to wet ball mills includes tumbling, vibratory, planetary and agitation. While it is possible to form submicron particles with each of these types of mills, the agitation or agitator ball mill is typically most efficient.

The agitator ball mill, also known as an attrition or stirred mill, has several advantages including high energy efficiency, high solids handling, narrow size distribution of the product output, and the ability to produce homogeneous slurries. The major variables in using an agitator ball mill are agitator speed, suspension flow rate, residence time, slurry viscosity, solid size of the in-feed, milling media size and desired product size. As a general rule, agitator mills typically grind particles to a mean particle size approximately $1/1000$ of the size of the milling media in the most efficient operation. In order to obtain mean particle sizes on the order of 0.05 $\mu$m to 0.5 $\mu$m, milling media having a size of less than 0.45 mm can be used. Milling media having diameters of about 0.2 mm and about 0.6 mm are available from Tosoh Ceramics, Bound Brook, N.J. Thus, to optimize milling, it is desirable to use a milling media approximately 1000 times the size of the desired particle. This minimizes the time required for milling.

Previously, the use of a milling process to achieve such fine particle sizes was difficult due to contamination of the slurry by the milling media. By using yttria stabilized zirconia (YTZ or Y-TZP, where TZP is tetragonal zirconia polycrystal) the contamination by spalling from the milling media and abrasion from the mill is minimized. Y-TZP has a fine grain, high strength and a high fracture toughness. High strength Y-TZP is formed by sintering at temperatures of about 1550° C. to form tetragonal grains having 1–2 $\mu$m tetragonal grains mixed with 4–8 $\mu$m cubic grains and high strength (1000 MPa), high fracture toughness (8.5 MPa $m^{1/2}$) and excellent wear resistance. The use of Y-TZP provides a suitable milling media for providing relatively pure structural fillers having mean particle sizes less than 0.5 $\mu$m. The YTZ milling media, however, is very expensive. So although agitator milling with YTZ milling media is time efficient, it is costly due to the expense of the milling media as well as the cost of the machine.

Furthermore, despite some reduction in contamination of the ground filler particulate by the use of YTZ milling media, agitator ball mills still introduce an unacceptably high level of contamination into dental composites containing the ground filler. The high intensity of the grinding action produced by the agitator, and the high momentum of the media, result in abrasion and spalling of the grinding chamber wall.

Vibratory ball mills are often used for submicron particle grinding because they provide a high production rate at low capital cost, fine and uniform product size distribution, low power consumption, and low contamination. The rate of milling is a function of the shape and size of the media. Cylindrical media are generally preferred, according to Engineered Materials Handbook®, Desk Edition, ASM International, p 742 (1995), because they spin on an axis and therefore produce small shear forces. The major variables in using a vibratory mill are the amplitude of vibration, energy developed in the mill, slurry viscosity, solid size of the in-feed, milling media size and desired product size.

Because vibratory milling involves low intensity grinding, abrasion and spalling of the grinding chamber wall and the milling media are less of a concern, as compared to agitator mills.

The vibratory mill has not previously been found useful for low contamination grinding of particles having a size less than the wavelength of light. U.S. Pat. No. 4,544,359 describes a dental restorative material with a borosilicate glass/barium silicate filler having an average particle size diameter of from about 0.5 $\mu$m to 5.0 $\mu$m. The filler is ground by a conventional wet milling process, such as vibratory milling, using a grinding or milling media such as low alumina, porcelain balls, stainless steel balls, borosilicate glass rods, or any other low alumina, non-contaminating grinding medium. Thus, there is a need for a low contamination, vibratory grinding mill and method to produce particles having a mean particle size of less than 0.5 $\mu$m.

SUMMARY OF THE INVENTION

The present invention is directed to a vibratory mill and method of use in which the vibratory mill has a grinding chamber charged with glass beads to provide substantially pure, contaminant-free, ground particles in the range of 0.05 $\mu$m–0.50 $\mu$m. The particles produced using the vibratory mill of the present invention may vary greatly in mean particle size; however, it has been discovered that particles having a mean particle size of between about 0.05 $\mu$m and about 0.5 $\mu$m provide the high strength required for load-bearing dental restorations, yet maintain a glossy appearance in clinical use required for cosmetic restorations. Further, the mill produces nonspherical particles which provide increased adhesion of the resin when used as filler in a dental composite, thereby further enhancing the overall strength of the composite. The filler particles ground with the mill of the present invention are highly pure and contaminant free, preferably having an average particle size less than the wavelength of visible light, that is less than about 0.50 $\mu$m. Highly pure, contaminant free, ground particles of various sizes and size distributions for uses other than dental composites may also be formed using the present invention.

The present invention, with glass bead media and optimized parameters, produces the particles of desired size, which are free of contamination and exhibit a narrow particle size distribution. The narrow particle size distribution minimizes the small percentage of particles above 0.5 $\mu$m which, when present, contribute to producing a non-glossy surface in clinical applications.

DETAILED DESCRIPTION OF THE INVENTION

The present invention, in a preferred form, is a vibratory mill, such as types M45-L (521 liter capacity) and M18-L (44 liter capacity) available from Sweco, Florence, Ky., which have an abrasion resistant liner of polyurethane on the grinding chamber.

Figure 1:
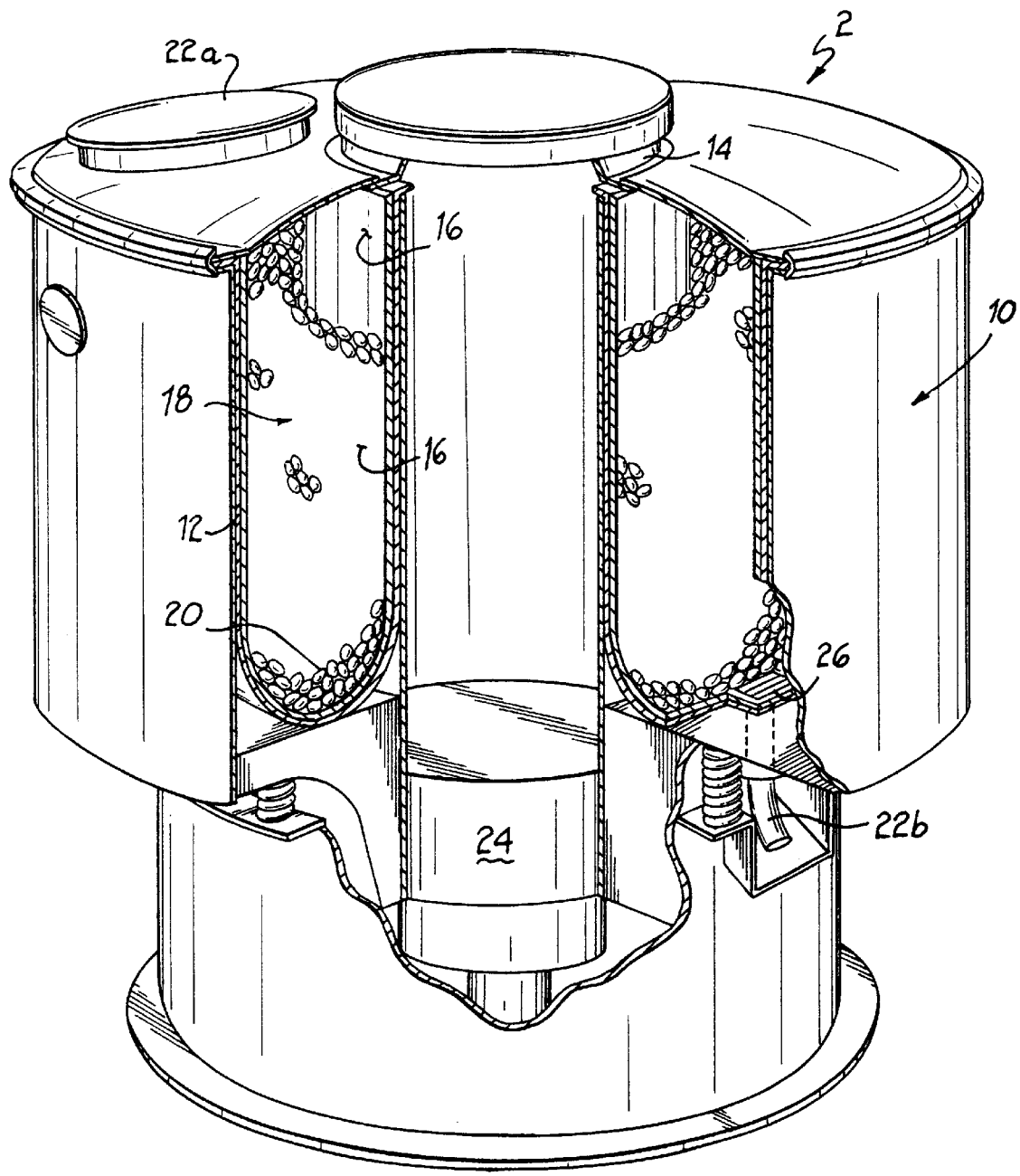
FIG. 1 is a plan view of a vibratory mill of the present invention.

As seen in FIG. 1, the vibratory mill 2 of the present invention includes a generally cylindrically shaped outer housing 10 supporting an inner housing 12, which is also generally cylindrically shaped but forms an annular ring about a center column 14. The inner housing 12 carries a polymer lining 16 of a type described hereinafter to prevent abrasion of inner housing 12. The inner housing 12 with the polymer lining 16 generally define the grinding chamber 18. The grinding chamber 18 is charged with milling media 20 of a type described hereinafter. Grinding chamber 18 is supplied with material to be ground by slurry inlet 22a and slurry is removed from the grinding chamber by slurry outlet 22b. The grinding chamber 18 vibrates in an up and down motion with an amplitude of approximately ¼ inch by means of a motor 24 equipped with appropriate centric weights, thereby imparting motion to the milling media 20 to grind the particle slurry. The slurry outlet 22b may include a media retainer 26 in fluid communication with slurry outlet 22b. The media retainer 26 allows the slurry to pass out of the vibratory mill through slurry outlet 22b, while retaining the media 20 within the grinding chamber 18. For larger capacity vibratory mills, such as a 521 liter capacity M45-L mill, circulation of the slurry from the top to the bottom of the chamber with a pump may be necessary for ensuring homogeneity of the slurry during grinding.

The milling media 20 of the present invention are glass beads, preferably soda lime glass beads, such as Dragonite Type LFK glass beads (Jaygo Inc., Union, N.J.). These beads are available in a diameter range of 0.1 mm to 10.0 mm, but 2 mm to 8 mm sized beads are preferred. In the case of agitator milling, smaller sized beads are generally preferred, but with vibratory milling, better results appear to be obtained with larger sized beads, albeit with longer grinding times. Beads are preferably spherically shaped, however, beads of other shapes with corresponding dimensions of those of spherically shaped beads can also be utilized, such as oblate spheroids or cylinders.

Although abrasion and spalling of the interior housing or wall 12 of the grinding chamber 18 is less likely in vibratory milling due to the low intensity nature of the grinding, it is still preferable to coat the interior 12 with a polymer lining 16 to prevent any abrasion that might occur. Pigment from a pigmented polymer lining has been found to contaminate the structural filler ground in the agitator mill, and thus, the resulting dental composite. Thus, a non-pigmented or clear polymer is applied to the inner surface of the grinding chamber, of the vibratory mill preferably at a thickness of at least 0.005 inches, to prevent contamination of the structural filler. Although the likelihood of abrasion of the polymer lining is less in the vibratory mill, it is nonetheless preferable to use a non-pigmented or clear polymer lining on the interior of the grinding chamber of the vibratory mill of the present invention.

The vibratory mill of the present invention is especially useful in forming particles with a desired mean particle size between about 0.05 $\mu$m and about 0.50 $\mu$m to be used as the structural filler in dental restorations. Structural fillers suitable for use in the present invention include barium magnesium aluminosilicate glass, barium aluminoborosilicate glass, amorphous silica; silica-zirconia; silica-titania; silica titania barium oxide, quartz, alumina and other inorganic oxide particles.

In order to provide ground particles having a mean particle size of less than 0.5 $\mu$m, the mill of this invention extensively comminutes the particles. Comminution provided by the mill of this invention deagglomerates the ground particles by separating particles from clusters, decreases the size of the particles, eliminates large particles by breakage and increases the specific surface area of the particles by producing a large quantity of very fine particles. Size reduction with the vibratory mill of this invention occurs due to a combination of: impact with the milling media, abrasion with the milling media and attrition of the particles. The vibratory mill of this invention uses a charge of glass beads as the milling media, which produces highly pure particulate of about 0.05 μm to about 0.5 μm mean particle size in about 40 to about 150 hours at a very low cost.

EXAMPLES

To prepare a structural filler for inclusion into a dental composite, 3 kg. of the filler material to be milled, such as barium aluminoborosilicate glass (for example, type SP-345, Specialty Glass, Oldsmar Fla. or type GM27884, Schott Glasswerke, Landshut, Germany), is charged into a 44 liter total capacity vibratory mill (available from Sweco, Florence, Ky., type M18-L) having a clear polyurethane clad grinding chamber and containing 110 lbs. of Dragonite glass beads from Jaygo, Inc. as the milling media. Four separate tests were run using different sized glass beads. Test A used 2.0 mm diameter glass beads, Test B used 4.0 mm diameter glass beads, Test C used 6.0 mm diameter glass beads, and Test D used 8.0 mm diameter glass beads. After charging the mill with the glass filler particles, the mill is filled with water up to 10 mm above the surface of the beads. The mill was then vibrated to comminute the particles. During the milling process, rough edges and facets were created on the structural filler particles by the impact with the milling media, abrasion with the milling media and attrition of the particles. Each of these edges provide an adhesion site for the resin which increases the overall strength of the cured composite. These edges are visible in FIGS. 2A and 2B.

When the filler slurry is removed from the mill, the mean particle size is measured, typically by laser scattering. Laser scattering is a method of measuring mean particle size by sensing the average relative angular intensity of scattered light. A beam of monochromatic light with a uniform wave front is directed at the sample, the light is diffracted or scattered by the particles and a detector is used to measure the relative average intensity of the scattered light at various angles. The mean particle size and size distribution may then be calculated from the relative average intensity. One such laser scattering device is disclosed in U.S. Pat. No. 5,610,712 to Schmitz et al., incorporated herein by reference in its entirety. For the present example, a Horiba Model 2A-910 Laser Scattering Mean Particle Size Analyzer was used. The particle size range of the structural fillers prepared by the above-described method is set forth in TABLES 1–4. TABLE 2 shows, for example, that for type SP345 barium aluminum silicate glass ground for. 144 hours with 4.0 mm diameter glass beads, 10 percent by volume of the filler particles have a mean particle size of less than 0.26 μm; 50 percent by volume of the filler particles have a mean particle size less than 0.45 μm; and 90 percent by volume of the filler particles have a mean particle size less than 0.73 μm.

TABLE 1

Test A: 2.0 mm Diameter Glass Beads
Particle Sizes In Microns

| | Particulate Filler Type SP345 | | |
|---|---|---|---|
| Volume | 0 hrs. | 72 hrs. | 144 hrs. |
| 10% | 0.72 μm | 0.36 μm | 0.27 μm |
| 50% | 3.39 μm | 0.95 μm | 0.63 μm |
| 90% | 14.01 μm | 1.76 μm | 1.18 μm |

TABLE 2

Test B: 4.0 mm Diameter Glass Beads
Particle Sizes In Microns

| | Particulate Filler Type | | | | | |
|---|---|---|---|---|---|---|
| | SP345 | | | GM27884 | | |
| Volume | 0 hrs. | 96 hrs. | 144 hrs. | 0 hrs. | 48 hrs. | 96 hrs. |
| 10% | 0.72 μm | 0.33 μm | 0.26 μm | 1.46 μm | 0.28 μm | 0.26 μm |
| 50% | 3.39 μm | 0.79 μm | 0.45 μm | 10.42 μm | 0.58 μm | 0.42 μm |
| 90% | 14.01 μm | 1.47 μm | 0.73 μm | 101.5 μm | 1.04 μm | 0.70 μm |

TABLE 3

Test C: 6.0 mm Diameter Glass Beads
Particle Sizes In Microns

| | Particulate Filler Type | | | | | | |
|---|---|---|---|---|---|---|---|
| | SP345 | | | GM27884 | | | |
| Volume | 0 hrs. | 48 hrs. | 84 hrs. | 0 hrs. | 36 hrs. | 84 hrs. | 120 hrs. |
| 10% | 0.72 μm | 0.29 μm | 0.27 μm | 1.46 μm | 0.31 μm | 0.26 μm | 0.24 μm |
| 50% | 3.39 μm | 0.57 μm | 0.45 μm | 10.42 μm | 0.67 μm | 0.45 μm | 0.36 μm |
| 90% | 14.01 μm | 0.99 μm | 0.75 μm | 101.5 μm | 1.28 μm | 0.77 μm | 0.60 μm |

TABLE 4

Test D: 8.0 mm Diameter Glass Beads
Particle Sizes In Microns

| | Particulate Filler Type SP345 | | |
|---|---|---|---|
| Volume | 0 hrs. | 48 hrs. | 120 hrs. |
| 10% | 0.72 μm | 0.30 μm | 0.25 μm |
| 50% | 3.59 μm | 0.60 μm | 0.41 μm |
| 90% | 14.01 μm | 1.11 μm | 0.71 μm |

As TABLES 1–4 above indicate, average particle sizes of below 0.5 μm can be achieved with a vibratory mill using glass beads as milling media. The difference in grinding times between the SP345 structural filler and the GM27884 structural filler is believed to be attributable to the difference in barium content. SP345 contains 30% barium, while GM27884 contains 25% barium. The lower content of barium makes the GM27884 filler particles harder and more fragile, and therefore easier to grind. With respect to the size of the glass beads, the grinding efficiency increases with increasing bead size going from 2 mm to 6 mm in diameter.

Thus can be attributed to higher momentum during impact playing a dominant role in the grinding mechanism. Essentially, no improvement in grinding efficiency is observed going from 6 mm to 8 mm in bead diameter. This may indicate that increased distance between contact points becomes an increasingly important factor compared to the weight of the bead.

Figure 2A:
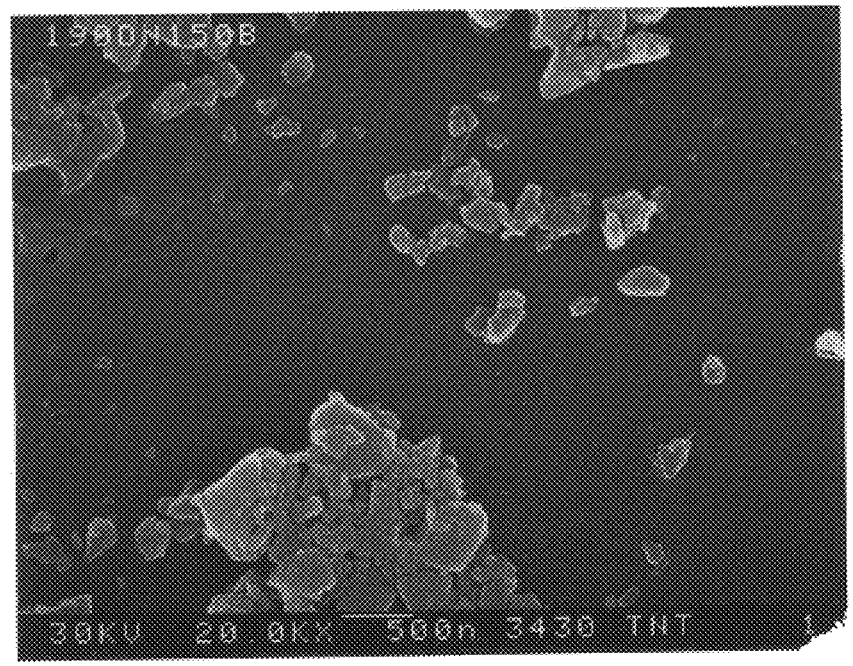
FIG. 2A is a scanning electron micrograph, at 20,000× magnification, of the particulate ground in the vibratory mill of the present invention.
Figure 2B:
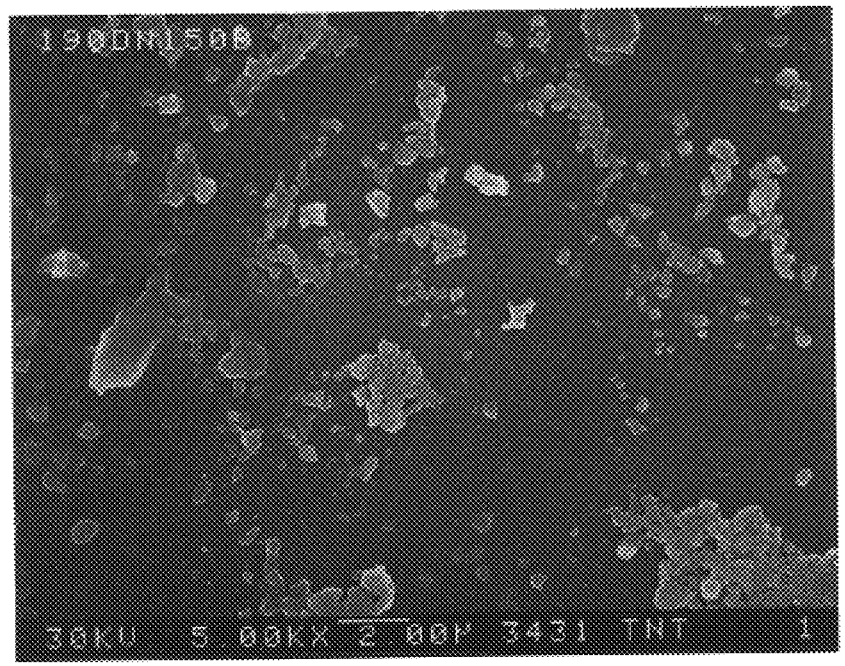
FIG. 2B is a scanning electron micrograph, at 5,000× magnification, of the particulate ground in the vibratory mill of the present invention.
Figure 3A:
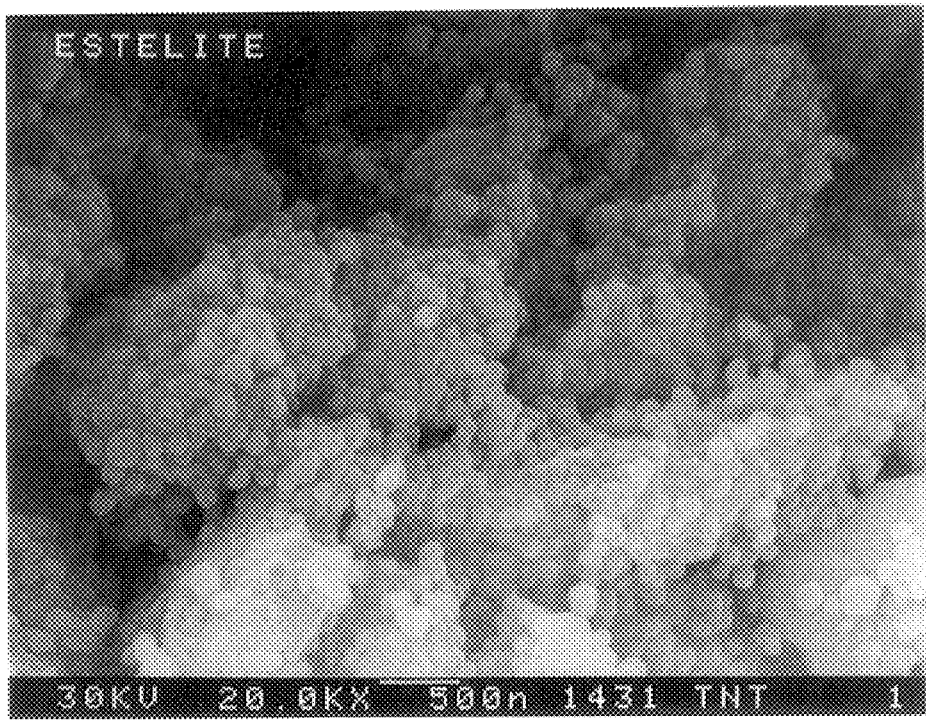
FIG. 3A is a scanning electron micrograph, at 20,000× magnification, of the prior art filler particles formed by sol-gel processes.
Figure 3B:
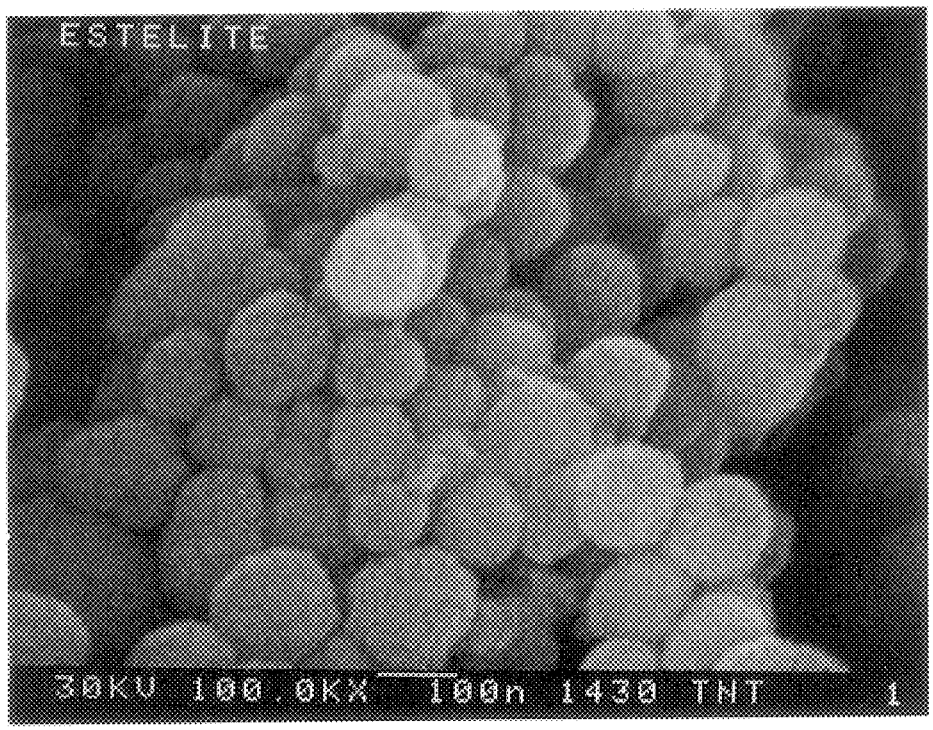
FIG. 3B is a scanning electron micrograph, at 100,000× magnification, of the prior art filler particles formed by sol-gel processes.

As shown in FIGS. 2A and 2B, the SP345 particulate ground in the vibratory mill of the present invention using 4.0 mm glass beads has the desired average particle size of less than about the average wavelength of visible light, and a narrow particle size distribution. As compared to the filler particles formed by the sol-gel processes, a shown in FIGS. 3A and 3B, the vibratory mill produces superior results. Furthermore, the results obtained with the vibratory mill are similar to results obtained with an agitator mill, except that the vibratory mill required significantly longer grinding times due to the low energy consumption nature of the vibratory mill. The cost of the glass bead milling media results, however, in low contamination grinding but at a significantly lower cost than the agitator mill using YTZ milling media. The dental composite produced using the particles ground by the vibratory mill of the present invention as a structural filler provide restorations having the high strength useful for load bearing restorations, and also provide good translucency and surface gloss, useful in cosmetic restorations. Various properties of dental composites using the structural filler prepared by an agitator mill were measured and reported in U.S. patent application Ser. No. 09/181,507, entitled "Optimum Particle Sized Hybrid Composite", C. Angeletakis, et al., filed on Oct. 28, 1998 now pending and incorporated herein by reference in its entirety. The gloss is apparent even after substantial wear as can be observed in a recall appointment 6 months or longer after the placement of the restoration. The ground particles produced by the vibratory mill of the present invention are expected to produce similar results. Through the use of structural filler particles ground using the vibratory mill of the present invention and having a average mean particle size less than about the average wavelength of visible light, a dental composite having high surface gloss and translucency with high strength may be formed.

While the present invention has been illustrated by a description of various embodiments and while these embodiments have been described in considerable detail, it is not the intention of the applicant to restrict or in any way limit the scope of the appended claims to such detail. Additional advantages and modifications will readily appear to those skilled in the art. For example, various sized glass beads can be used to grind the particulate to the desired size with variable grinding times but equal results with respect to size and low contamination. The invention, in its broader aspects, is therefore not limited to the specific details, representative composition as shown and described. This has been a description of the present invention, along with the preferred coating composition as currently known. However, the invention itself should only be defined by the appended claims.

What is claimed is:

1. A method for efficiently grinding submicron-sized dental filler particulate of high purity, comprising the steps of:

providing a vibratory mill having a grinding chamber;

charging the grinding chamber with glass beads having a diameter in the range of about 0.1 mm to about 10.0 mm;

charging the grinding chamber with a wet slurry containing the dental filler particulate to be ground;

vibrating the grinding chamber for a time sufficient to grind the particulate to a mean particle size of about 0.05 $\mu$m to about 0.50 $\mu$m; and separating the slurry from the milling media.

2. The method of claim 1, wherein the glass beads are soda lime glass beads.

3. The method of claim 1, wherein the glass beads have a diameter of about 2.0 mm to about 8.0 mm.

4. The method of claim 3, wherein the particulate is ground for about 40 hours to about 150 hours.

5. A method for efficiently grinding submicron-sized dental filler particulate of high purity, comprising the steps of:

providing a vibratory mill having a grinding chamber coated with a non-pigmented, abrasion resistant polymer coating;

charging the grinding chamber with glass beads having a diameter in the range of about 0.1 mm to about 10.0 mm;

charging the grinding chamber with a wet slurry containing the dental filler particulate to be ground;

vibrating the grinding chamber for a time sufficient to grind the particulate to a mean particle size of about 0.05 $\mu$m to about 0.50 $\mu$m; and separating the slurry from the milling media.

6. The method of claim 5, wherein the polymer coating is a polyurethane coating.

7. The method of claim 5, wherein the glass beads are soda lime glass beads.

8. The method of claim 5, wherein the glass beads have a diameter of about 2.0 mm to about 8.0 mm.

9. The method of claim 8, wherein the particulate is ground for about 40 hours to about 150 hours.

\* \* \* \* \*